(12) United States Patent
McDonald et al.

(10) Patent No.: US 9,005,634 B2
(45) Date of Patent: Apr. 14, 2015

(54) SHELF STABLE PHARMACEUTICAL DEPOT

(75) Inventors: Phillip E. McDonald, Hibbing, MN (US); Suping Lyu, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 200 days.

(21) Appl. No.: 13/282,532

(22) Filed: Oct. 27, 2011

(65) Prior Publication Data

US 2012/0263761 A1 Oct. 18, 2012

(30) Foreign Application Priority Data

Apr. 13, 2011 (WO) ................ PCT/US2011/032260

(51) Int. Cl.
| | | |
|---|---|---|
| *A61K 9/14* | (2006.01) | |
| *A61K 9/00* | (2006.01) | |
| *A61K 47/10* | (2006.01) | |
| *A61K 47/32* | (2006.01) | |
| *A61K 47/38* | (2006.01) | |
| *A61K 9/70* | (2006.01) | |
| *A61K 31/4168* | (2006.01) | |
| *A61K 31/445* | (2006.01) | |

(52) U.S. Cl.
CPC ............... *A61K 9/0024* (2013.01); *A61K 47/10* (2013.01); *A61K 47/32* (2013.01); *A61K 47/38* (2013.01); *A61K 9/7007* (2013.01); *A61K 31/4168* (2013.01); *A61K 31/445* (2013.01)

(58) Field of Classification Search
CPC ........................... A61K 9/0024; A61K 9/7007
See application file for complete search history.

(56) References Cited

U.S. PATENT DOCUMENTS

| | | | | |
|---|---|---|---|---|
| 2009/0264491 | A1* | 10/2009 | McKay et al. ................ | 514/401 |
| 2011/0123517 | A1* | 5/2011 | Gallagher et al. ......... | 424/94.64 |

FOREIGN PATENT DOCUMENTS

| | | |
|---|---|---|
| WO | 2004043432 A2 | 5/2004 |
| WO | 2006036280 A1 | 4/2006 |
| WO | 2009100441 A2 | 8/2009 |
| WO | 2009129439 A2 | 10/2009 |

OTHER PUBLICATIONS

International Search Report and Written Opinion for PCT/US2011/032260 the counterpart application mailed on Oct. 4, 2011, 12 pages.

\* cited by examiner

*Primary Examiner* — Brian Gulledge
(74) *Attorney, Agent, or Firm* — Sorell Lenna & Schmidt LLP

(57) ABSTRACT

A pharmaceutical depot includes a biodegradable polymer having a glass transition temperature of 20 degrees centigrade or less and at least 25% wt solid particles suspended in the biodegradable polymer. The pharmaceutical depot also includes a post-operative pain relieving therapeutic agent.

18 Claims, No Drawings

SHELF STABLE PHARMACEUTICAL DEPOT

BACKGROUND

This disclosure relates to pharmaceutical depots that contribute to the local treatment of pain and do not exhibit noticeable dimensional changes when stored.

Pain can be divided into two types: nociceptive pain and neuropathic pain. Acute nociceptive pain refers to pain experienced when tissue is being damaged or is damaged. Acute pain serves at least two physiologically advantageous purposes. First, it warns of dangerous environmental stimuli (such as hot or sharp objects) by triggering reflexive responses that end contact with the dangerous stimuli. Second, if reflexive responses do not avoid dangerous environmental stimuli effectively, or tissue injury or infection otherwise results, acute pain facilitates recuperative behaviors. For example, acute pain associated with an injury or infection encourages an organism to protect the compromised area from further insult or use while the injury or infection heals. Once the dangerous environmental stimulus is removed, or the injury or infection has resolved, acute pain, having served its physiological purpose, ends.

Post-operative pain is a result of a surgical procedure. Traditional surgical procedures for pathologies located deep within the body can cause significant trauma to the intervening tissues. These open procedures can often require a long incision, extensive muscle stripping, prolonged retraction of tissues, denervation and devascularization of tissue. Many of these surgeries require a recovery room time of several hours and several weeks of post-operative recovery time due to the use of general anesthesia and the destruction of tissue during the surgical procedure. In some cases, these invasive procedures lead to permanent scarring and chronic pain that can be more severe than the pain leading to the surgical intervention.

BRIEF SUMMARY

The present disclosure relates to shelf stable pharmaceutical depots. In particular, the present disclosure relates to shelf stable pharmaceutical depots that include biodegradable polyesters and a post-operative pain relieving therapeutic agent.

In one embodiment, a pharmaceutical depot includes a biodegradable polymer having a glass transition temperature of 20 degrees centigrade or less and at least 25% wt solid particles suspended in the biodegradable polymer. The pharmaceutical depot also includes a post-operative pain relieving therapeutic agent.

In another embodiment, a pharmaceutical depot includes a biodegradable polymer having a glass transition temperature in a range from of 0 to 15 degrees centigrade, at least 25% wt solid particles suspended in the biodegradable polymer, and a post-operative pain relieving therapeutic agent including clonidine.

In a further embodiment, a pharmaceutical depot includes a biodegradable polymer having a glass transition temperature in a range from of 0 to 15 degrees centigrade, at least 40% wt solid particles suspended in the biodegradable polymer, and a post-operative pain relieving therapeutic agent comprising clonidine. The solid particles have a particle size in a range from 50 to 100 micrometers.

These and various other features and advantages will be apparent from a reading of the following detailed description.

DETAILED DESCRIPTION

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure relates to shelf stable pharmaceutical depots. In particular, the present disclosure relates to shelf stable pharmaceutical depots that include biodegradable polyesters and a post-operative pain relieving therapeutic agent. Biodegradable polyester depots that include clonidine and certain excipients show improved dimensional stability at room temperatures with extended clonidine release profiles. While the present disclosure is not so limited, an appreciation of various aspects of the disclosure will be gained through a discussion of the examples provided below.

The shelf stable pharmaceutical depots include a biodegradable polymer and at least 25% wt solid particles suspended in the biodegradable polymer, and a post-operative pain relieving therapeutic agent. In many embodiments the pharmaceutical depot provides a long duration therapeutic agent release in vivo, for example, for at least 3 days, or for at least 5 days, or for at least 10 days or for at least 20 days, as desired.

The shelf stable pharmaceutical depots can be inserted in to a surgical wound to provide extended release of the post-operative pain relieving therapeutic agent. The shelf stable pharmaceutical depots provide effective space filling of the surgical wound and can evenly distribute the post-operative pain relieving therapeutic agent to all areas of the surgical wound space. In many embodiments the shelf stable pharmaceutical depot is a flexible film that can be laid into the surgical wound.

The biodegradable polymers can include polyesters that degrade over time in vivo. Biodegradable polyesters include, for example, polylactides, polyglycolides, polycaprolactone, copolymers thereof, terpolymers thereof, and any combinations thereof. In many embodiments the biodegradable polyester is a polylactide, a polyglycolide, a copolymer thereof, or a combination thereof. Commercially available biodegradable polymers include, for example, 5050 DLG 1A (Lactide-Glycolide Polymer MW=8K)—Lakeshore Biomaterials LP-342, 5050 DLG 4A—(Lactide-Glycolide Polymer MW=50K)—Lakeshore Biomaterials LP-389, and 5050

DLG 8E—(Lactide-Glycolide Polymer MW=130K)—Lakeshore Biomaterials LX00195-156, ground with Retsch Mill<80 um sieve.

In many embodiments the biodegradable polymers includes a plasticizer such as polyethylene glycol, for example. The combination of the biodegradable polymer and the plasticizer can form a biodegradable polymer having a glass transition value in a range from 0 to 25 degrees centigrade, or in a range from 0 to 15 degrees centigrade, or in a range from 0 to 15 degrees centigrade.

The pain relieving therapeutic agent can be any useful therapeutic agent that reduces or mitigates pain, when administered to a subject. In many embodiments the pain relieving therapeutic agent is a post-operative pain relieving therapeutic agent. The post-operative pain relieving therapeutic agent can be any useful agent that relieves or is indicated for relieving post-operative pain. Illustrative post-operative pain relieving therapeutic agents include, for example, local anesthetics and alpha or beta adrenergic agonists.

Local anesthetics includes, for example, benzocaine chloroprocaine, cocaine, cyclomethycaine, dimethocaine/ tarocaine, propoxycaine, procaine/novocaine, proparacaine, tetracaine/amethocaine, articaine, bupivacaine, carticaine, cinchocaine/dibucaine, etidocaine, levobupivacaink, lidocaine/lignocaine, mepivacaine, piperocaine, prilocaine, ropivacaine, and trimecaine. In many embodiments the local anesthetic is bupivacaine. The local anesthetic can be present in the flowable pharmaceutical depot in any therapeutic amount such as, for example, from 5 to 60%, or from 10 to 50% by weight.

Alpha or beta adrenergic agonists include for example, dobutamine, isoproterenol, salbutamol, fenoterol, formoterol, isoproterenolm, metaproterenol, salmeterol, terbutaline, clenbuterol, methoxamine, methylnorepinephrine, oxymetazoline, phenylephrine, clonidine, guanfacine, guanabenz, guanoxabenz, guanethidine, xylazine, and methyldopa. In many embodiments the alpha or beta adrenergic agonist is clonidine. The alpha or beta adrenergic agonist can be present in the flowable pharmaceutical depot in any therapeutic amount such as, for example, from 0.01 to 10%, or from 0.1 to 5% by weight.

Certain excipients or solid particles suspended in the biodegradable polymer improved the dimensional stability of the pharmaceutical depot at room temperatures. In many embodiments the pharmaceutical depot included at least 25% wt excipients or solid particles, or at least 40% wt excipients or solid particles, or at least 50% wt excipients or solid particles, or in a range from 25 to 50% wt excipients or solid particles. The excipients or solid particles can be hydrophobic or hydrophilic, or a combination thereof.

Hydrophilic excipients include dextran I, dextran III, mannitol, polyvinylpyrrolidone (PVP), hydroxyproplymethyl cellulose (HPMC), chitosan, for example. Hydrophobic excipients include $MgCO_3$, $CaCO_3$, cellulose acetate propionate, ethyl cellulose and hydroxyapatite, for example. Particle size of the excipients or solid particles in the range from 40 to 120 micrometers or from 50 to 100 micrometers provided improved dimensional stability of the pharmaceutical depot at room temperatures,

EXAMPLES

Unless otherwise noted, all starting materials are commercially available from the Sigma Aldrich Chemical Company, Incorporated, Milwaukee Wis. (Aldrich).

Materials

Clonidine HCl—Spectrum Chemicals (Gardena, Calif.), Spray Dried with Buchi at S&T, 10-20 um Bupivacaine Base—Orgamol #971526—BASF Chemical Company 5050 DLG 1A (Lactide-Glycolide Polymer MW=8K)—Lakeshore Biomaterials LP-342, ground with Retsch Mill <8 um sieve 5050 DLG 4A—(Lactide-Cllycolide Polymer MW=50K)—Lakeshore Biomaterials LP-389, ground with Retsch Mill <80 um sieve 5050 DLG 8E—(Lactide-Glycolide Polymer MW=130K)—Lakeshore Biomaterials LX00195-156, ground with Retsch Mill<80 um sieve Methoxypoly(ethylene glycol)—mPEG 550—Sigma Aldrich mannitol—Sigma Aldrich M9546

$MgCO_3$—Sigma Aldrich

Chitosan Low MW—Sigma Aldrich 448869

Cellulose acetate propionate—Sigma Aldrich

Hydroxyapatite—Sigma Aldrich 289396

$CaCO_3$—SigmaUltra C4830—Sigma Aldrich

Demineralized Bone <100 um—bovine

Hydroxypropyl methyl cellulose (HPMC)—Sigma Aldrich 442755

Ethyl cellulose—Sigma Aldrich 247499

Dextrin Type I—Sigma Aldrich

Dextrin Type III—Sigma Aldrich

Polyvinyl pyrrolidone (PVP)—Sigma Aldrich

Polymer Milling:

Approximately 100 grams of polymer was placed in a polypropylene beaker and cooled with liquid nitrogen (approx 200 mL) for 10 minutes. The polymer was then ground into fine particles consisting of 80 microns or less using a Retsch Centrifugal Mill (Type/model ZM 200). The ground polymer particles were collected and placed in 10 cm aluminum weigh pans. The pans were placed in a vacuum oven at 35° C. under vacuum for 24 hours to remove any condensation resulting from the grinding process.

Spray Dried Drug:

Clondine HCl was dissolved in methanol to yield a 12% (w/w) solution. The solution was spray dried in a Buchi B-290 Mini Spray Dryer (Bilotti Laboratorium AG, Switzerland) using a 1120 kHz Sono-Tek ultrasonic nozzle (Sono-Tek Corp., Milton, N.Y.). The processing parameters were set as follows: inlet temp. (70° C.), aspirator (80%), nitrogen inlet (50 mm), spray flow rate (80 mL/hr) and ultrasonic generator (0.8 watts). The spray dried powder was collected and dried for additional 24 hours at 70° C. and 15 mmHg vacuum.

Melt Extrusion:

Polymer powder and mPEG were dry mixed with a spatula until mPEG was coated with polymer. Then excipient (if any) was added and mixed with a spatula. Pre-mixed formulations were loaded into a Haake Mini-Lab twin screw extruder (Thermo Fischer Scientific, Waltham, Mass.) set at 85-130° C. and 30 RPM. A 5-7 gram batch was extruded out of a 1.5 mm diameter. Then 3 grams of the extruded formulation is loaded into the Dynisco Laboratory Mixer Molder pre-heated to the same temperature as the extrusion run. The drug was added on top of the material and the spindle was rotating at max RPM. Mix for 2-3 minutes, lifting/lowering the spindle then extrude out the bottom. Load material back into cup and repeat process 2× to insure proper mixing.

Each formulation was placed between two armalon sheets and pressed using the Carver Heat Press set at 70-90° C. Stainless steel washers were used as shims in order to achieve desired film thickness.

In-Vitro Drug Release:

Each formulation was tested in triplicate and cut by a razor blade to 20×5×0.5 mm. Each cut film was placed in 5 mL of phosphate buffer solution at pH 7.4 in a 20 mL scintillation vial and incubated at 37 degree centigrade and 60 RPM. At pre-selected times, the buffer was removed and analyzed for drug content by HPLC. Then, each vial was replaced with fresh buffer and placed back in the incubator.

Visual Creep Test:

The melt extruded formulations were placed in a 20 mL vial and set in the nitrogen purged isolator hood for several days at room temperature. Formulations were ranked as pass or fail depending on how the formulations had moved during the time period. A pass ranking was given if the formulations had not changed and a fail ranking was given if the formulations had noticeable deformation or flow such as sharp edges becoming round or severely sticking to the glass.

Drug Particle Sizing:

Clonidine HCl was suspended in acetone to yield a cloudy suspension (~10 mg/4 mL). Ethyl cellulose and cellulose acetate propionate were suspended in phosphate buffer with 0.5 wt % sodium dodecyl sulfate. Demineralized bone, chitosan, MgCO3, CaCO3, and hydroxyapatite were suspended in water. HPMC, mannitol, and dextrin was suspended in acetone and PVP was suspended in mineral oil. The suspension was pipetted into the fraction cell holder for the Horiba Instruments Partica LA-950 Laser Diffraction Particle Size Analyzer until the % transmittance reached 80-90%.

Results

The formulations tested are summarized in Table 1 and both visual creep and drug release results are summarized in Table 2. AH formulations (except Formulation ID #6) included 0.5% wt clonidine and had glass transition temperatures in a range from 5 to 15 degrees centigrade.

TABLE 1

Formulation Compositions

| Formulation ID | Wt % Excipient | Wt % Polymer | Wt % mPEG |
|---|---|---|---|
| 1 | 30% MgCO3 | 61.5% 5050DLG 1A | 8% |
| 2 | 50% Dextran I | 41.5% 5050DLG 1A | 8% |
| 3 | 50% Dextran III | 41.5% 5050DLG 4A | 8% |
| 4 | 50% manitol | 37.5% 5050DLG 8E | 12% |
| 5 | 50% manitol | 39.5% 5050DLG 4A | 10% |
| 6 | 50% bupivacaine | 42% 5050DLG 1A | 8% |
| 7 | 40% MgCO3 | 51.5% 5050DLG 1A | 8% |
| 8 | 50% PVP | 39.5% 5050DLG 4A | 10% |
| 9 | 50% PVP | 39.5% 5050DLG 8E | 10% |
| 10 | 50% Hydroxyapatite | 39.5% 5050DLG 1A | 10% |
| 11 | 25% manitol 25% CaCO3 | 40% 5050DLG 4A | 10% |
| 12 | 25% manitol | 59.5% 5050DLG 4A | 15% |
| 13 | 25% manitol | 59.5% 5050DLG 8E | 15% |
| 14 | 50% HPMC | 38% 5050DLG 8E | 12% |
| 15 | 26% mannitol | 58.5% 5050DLG 4A | 15% |
| 16 | 50% HPMC | 39.5% 5050DLG 4A | 10% |

TABLE 2

Formulation Results

| Formulation ID | Visual Creep Test | Drug Elution Summary |
|---|---|---|
| 1 | Fail | 10% 1 day burst; 14 day duration |
| 2 | Pass | 100% 1 day burst |
| 3 | Pass | 100% 1 day burst |
| 4 | Pass | 100% 1 day burst |
| 5 | Pass | 100% 1 day burst |
| 6 | Pass | 20% 1 day burst; 12 day duration |
| 7 | Fail | 10% 1 day burst; 8 day duration |
| 8 | Pass | 100% 1 day burst |
| 9 | Pass | 100% 1 day burst |
| 10 | Fail | 40% 1 day burst; 4 day duration |
| 11 | Fail | 55% 1 day burst; >14 day duration |
| 12 | Fail | 55% 1 day burst; 6 day duration |
| 13 | Pass | 80% 1 day burst; 3 day duration |
| 14 | Pass | 70% 1 day burst; 3 day duration |
| 15 | Fail | 25% 1 day burst; 10 day duration |
| 16 | Pass | 50% 1 day burst; 10 day duration |

For the most part, the hydrophilic excipients at 50% loading (dextran I, III, mannitol, PVP, & HPMC) released the drug in one day. Also, the effect of using the 4A vs. the SE did not have an effect on drug release at 50% loading. The release can be slowed down when lowering the loading to 25% mannitol; however, the molecular weight of the polymer (SE vs. 4A) does have an effect on the drug release rate. The one exception in the bunch is 50% HPMC which did show a more controlled release. The 1 day burst was still high and the 8E did release drug faster than the 4A.

The hydrophobic excipients (MgCO3, CaCO3, hydroxyapatite) all had good drug release profiles, but failed the visual creep test. The formulations generally passing the visual creep test typically had average particle sizes ranging from 50-100 micrometers and were 50 wt % composition of the total formulation.

Thus, embodiments of the SHELF STABLE PHARMACEUTICAL DEPOT are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. A pharmaceutical depot comprising:
   a biodegradable polymer having a glass transition temperature of 20 degrees centigrade or less, the biodegradable polymer comprising poly(D,L-lactide-co-glycolide) thereof;
   solid particles of mannitol in an amount of at least 40% by weight suspended in the biodegradable polymer, the solid particles have a particle size in a range from 50 to 100 micrometers and the pharmaceutical depot comprises methoxypoly(ethylene glycol); and
   a post-operative pain relieving therapeutic agent in an amount of between 0.01 and 10% by weight.

2. A pharmaceutical depot according to claim 1, wherein the post-operative pain relieving therapeutic agent is a clonidine.

3. A flowable pharmaceutical depot according to claim 1, wherein the solid particles further comprise hydrophobic solids.

4. A pharmaceutical depot according to claim 1, wherein the solid particles comprise hydrophilic solids.

5. A pharmaceutical depot according to claim 1, wherein the solid particles further comprise hydroxypropylmethyl cellulose.

6. A pharmaceutical depot according to claim 1, wherein the solid particles have a particle size in a range from 50 to 100 micrometers.

7. A pharmaceutical depot according to claim 1, wherein the biodegradable polymer having a glass transition temperature in a range from 0 to 15 degrees centigrade.

8. A pharmaceutical depot comprising:
a biodegradable polymer having a glass transition temperature in a range from of 0 to 15 degrees centigrade, the biodegradable polymer comprising poly(D,L-lactide-co-glycolide);
solid particles comprising mannitol in an amount of 25-50% by weight suspended in the biodegradable polymer and the pharmaceutical depot comprises methoxypoly(ethylene glycol); and
a post-operative pain relieving therapeutic agent comprising clonidine in an amount of between 0.01 and 10% by weight.

9. A pharmaceutical depot according to claim 8, wherein the pharmaceutical depot comprises at least 40% wt solid particles suspended in the biodegradable polymer.

10. A flowable pharmaceutical depot according to claim 8, wherein the solid particles comprise hydrophobic solids.

11. A pharmaceutical depot according to claim 8, wherein the solid particles further comprise hydrophilic solids.

12. A pharmaceutical depot according to claim 8, wherein the solid particles further comprise hydroxypropylmethyl cellulose.

13. A pharmaceutical depot comprising:
a biodegradable polymer having a glass transition temperature in a range from of 0 to 15 degrees centigrade, the biodegradable polymer comprising poly(D,L-lactide-co-glycolide);
solid particles comprising mannitol in an amount of 40-50% by weight suspended in the biodegradable polymer, the solid particles have a particle size in a range from 50 to 100 micrometers and the pharmaceutical depot comprises methoxypoly(ethylene glycol); and
a post-operative pain relieving therapeutic agent comprising clonidine in an amount of between 0.01 and 10% by weight.

14. A pharmaceutical depot according to claim 13, wherein the solid particles comprise hydroxypropylmethyl cellulose.

15. A pharmaceutical depot according to claim 1, wherein the pharmaceutical depot is in the form of a flexible film configured to be laid into a surgical site.

16. A pharmaceutical depot according to claim 8, wherein the pharmaceutical depot is in the form of a flexible film configured to be laid into a surgical site.

17. A pharmaceutical depot according to claim 8, wherein the mannitol is in the depot in an amount of 50% w/w and the methoxypoly(ethylene glycol) is in the depot in an amount of 10% w/w and the depot releases 100% of the clonidine in one day.

18. A pharmaceutical depot according to claim 8, wherein the mannitol is in the depot in an amount of 25% w/w and the methoxypoly(ethylene glycol) is in the depot in an amount of 15% w/w and the depot releases 80% of the clonidine in one day.

\* \* \* \* \*